US008835414B2

(12) United States Patent
Fernández et al.

(10) Patent No.: US 8,835,414 B2
(45) Date of Patent: Sep. 16, 2014

(54) TREATMENT OF VAGINAL ATROPHY IN WOMEN WITH CARDIOVASCULAR PATHOLOGY RISK

(75) Inventors: Álvaro Acebrón Fernández, Madrid (ES); Dolores Blanco Lousame, Madrid (ES); Jaime Moscoso Del Prado, Madrid (ES); Concepción Nieto Magro, Madrid (ES)

(73) Assignee: ITF Research Pharma S.L.U., Alcobendas, Madrid ( * ) Notice: Subject to any disclaimer, the term of this patent is extended or adjusted under 35 U.S.C. 154(b) by 0 days.

(21) Appl. No.: 13/140,602

(22) PCT Filed: Aug. 7, 2009

(86) PCT No.: PCT/EP2009/060304
§ 371 (c)(1),
(2), (4) Date: Aug. 8, 2011

(87) PCT Pub. No.: WO2010/069621
PCT Pub. Date: Jun. 24, 2010

(65) Prior Publication Data
US 2011/0312929 A1 Dec. 22, 2011

(30) Foreign Application Priority Data

Dec. 19, 2008 (ES) .................................. 200803623

(51) Int. Cl.
*A61K 31/56* (2006.01)
*A61K 47/32* (2006.01)
*A61K 31/566* (2006.01)
*A61K 9/00* (2006.01)

(52) U.S. Cl.
CPC .............. *A61K 31/566* (2013.01); *A61K 47/32* (2013.01); *A61K 9/0034* (2013.01)
USPC ....................................................... 514/182

(58) Field of Classification Search
USPC ....................................................... 514/182
See application file for complete search history.

(56) References Cited

U.S. PATENT DOCUMENTS

| | | | |
|---|---|---|---|
| 3,159,543 A | 12/1964 | Ercoli et al. | |
| 5,340,586 A * | 8/1994 | Pike et al. | 424/426 |
| 5,719,197 A | 2/1998 | Kanios et al. | |
| 5,894,019 A | 4/1999 | Hesse et al. | |
| 5,942,243 A | 8/1999 | Shah | |
| 2003/0022877 A1 | 1/2003 | Dudley | |
| 2006/0240111 A1 * | 10/2006 | Fernandez et al. | 424/487 |

FOREIGN PATENT DOCUMENTS

| | | | |
|---|---|---|---|
| EP | 0431719 B1 | 11/1994 | |
| EP | 0770384 | 2/1997 | |
| EP | 0719146 B1 | 12/1998 | |
| EP | 0818194 B1 | 1/2002 | |
| EP | 0784466 B1 | 2/2002 | |
| EP | 1325752 A2 | 7/2003 | |
| EP | 1872775 A1 * | 2/2008 | |
| EP | 1652535 B1 | 9/2010 | |
| ES | 2171589 | 9/2002 | |
| WO | 8502092 A1 | 5/1985 | |
| WO | 9106289 A1 | 5/1991 | |
| WO | 9629056 A1 | 9/1996 | |
| WO | 9715314 A1 | 5/1997 | |
| WO | 9805303 A1 | 2/1998 | |
| WO | 9820872 A1 | 5/1998 | |
| WO | 9913862 A2 | 3/1999 | |
| WO | 0047144 A1 | 8/2000 | |
| WO | 0050078 A1 | 8/2000 | |
| WO | 0124788 A2 | 4/2001 | |
| WO | 0128515 A1 | 4/2001 | |
| WO | 03003782 A1 | 1/2003 | |
| WO | 2007021805 | 2/2007 | |
| WO | 2007070067 | 6/2007 | |
| WO | 2007085020 A2 | 7/2007 | |
| WO | 2008089405 | 7/2008 | |
| WO | 2009000954 A2 | 12/2008 | |

OTHER PUBLICATIONS

Nachtigall, et al., Menopause Management (2005); 17-19.*
Simon et al. Supplement to OBG management 2010 (2010); 51-S25.*
Haaften et al J. steroid Biochem. vol. 33, No. 4A, pp, 647-653, 1989.*
Barentsen et al., "Continuous low dose estradiol released from a vaginal ring versus estriol vaginal cream for urogenital atrophy", Eur J. of Obstet. Gynecol. Repord. Bio; 71: 73-80 (1997).
Blanco-Fuente et al., "In-vitro bioadhesion of carbopol hydrogels", Int. J. of Pharm.; 142: 169-174 (1996).
Bottiglione et al., "Transvaginal estriol administration in postmenopausal women: a double blind comparative study of two different doses", Maturitas; 22: 227-232 (1995).
Dessole et al., "Efficacy of low-dose intravaginal estriol on urogenital aging in postmenopausal women", Menopause: The J. of the North American Menopause Society; 11(1): 49-56 (2004).
Foidart et al., "Efficacy of sustained-release vaginal oestriol in alleviating urogenital and systemic climacteric complaints", Maturitas; 13: 99-107 (1991).
Gerbaldo et al., "Endometrial morphology after 12 months of vaginal oestriol therapy in post-menopausal women", Maturitas; 13: 269-274 (1991).
Iosif, C.S., "Effects of protracted administration of estriol on the lower genito urinary tract in postmenopausal women", Arch. Gynecol. Obstet.; 251: 115-120 (1992).
Katz et al., "The Effects of Estradiol and Estriol on Plasma Levels of Cortisol and Thyroid Hormone-Binding Globulins and on Aldosterone and Cortisol Secretion Rates in Man", The J. of Clinical Investigation; 46(11): 1768-1777 (1967).

(Continued)

*Primary Examiner* — Shirley V Gembeh
(74) *Attorney, Agent, or Firm* — Hoffmann & Baron, LLP

(57) ABSTRACT

The present invention relates to the use of estriol in the preparation of a pharmaceutical formulation for vaginal administration with the capacity to self-limit the absorption of estriol, for the prevention and/or the treatment of urogenital atrophy in women said women having a high probability of suffering from a cardiovascular pathology or suffering or having suffered from a cardiovascular pathology.

24 Claims, 1 Drawing Sheet

(56) References Cited

OTHER PUBLICATIONS

Kicovic et al., "The treatment of postmenopausal vaginal atrophy with ovestin vaginal cream or suppositories: clinical, endocrinological and safety aspects", Maturitas; 2: 275-282 (1980).
Ovestin Cream Leaflet; Patient Information Leaflet (PIL) for Ovestin Cream, Dec. 1, 2005.
Palacios et al., "Low-dose, vaginally administered estrogens may enhance local benefits of systemic therapy in the treatment of urogenital atrophy in postmenopausal women on hormone therapy", Maturitas; 50: 98-104 (2005).
Pinkerton et al., "Alternatives to the Use of Estrogen in Postmenopausal Women", Endocrine Reviews; 20(3): 308-320 (1999).
Puck et al., "Die Wirkung des Oestriol auf Corpus uteri, Cervix uteri und Vagina der Frau", Deutsche Medizinische Wochenschrift: 82: 1864 (1957).
Samsioe, G, "Cardioprotection by estrogens: mechanisms of action—the lipids", Int. J. of Fer. and Menopausal Studies; 39(1): 43-49 (1994).
Summary of Product Characteristics, SPC Ovestin Cream (Sep. 1995).
Tamburic et al., "A comparison of different in vitro methods for measuring mucoadhesive performance", Eur. J. of Pharmaceuticals and Biopharmaceutics; 44: 159-167 (1997).
USP NF, The Official Compendia of Standards: 2521-2522 (2002).
G. Creatsas et al., Maturitas 2005, 52, 32-37, cited in the first Office Action by the European Examiner.

* cited by examiner

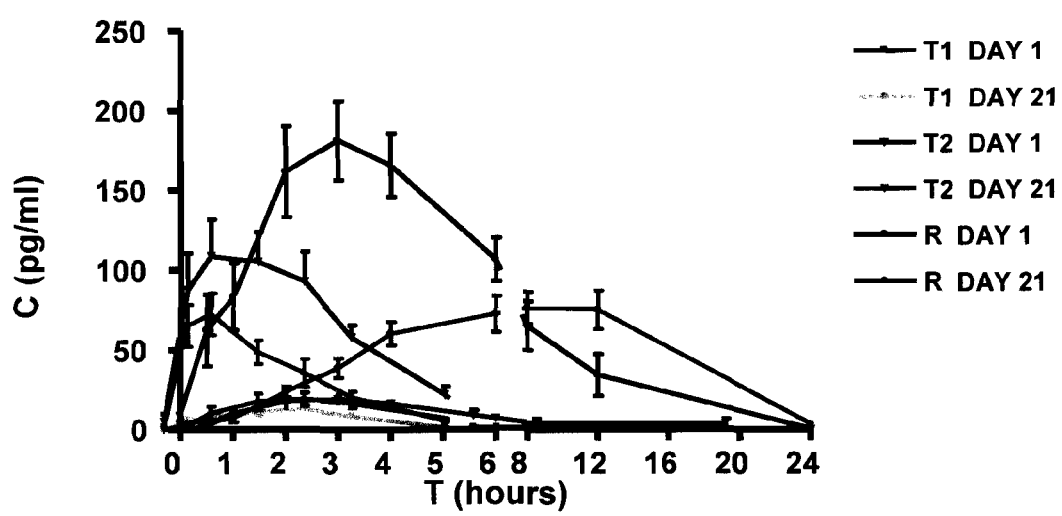

TREATMENT OF VAGINAL ATROPHY IN WOMEN WITH CARDIOVASCULAR PATHOLOGY RISK

CROSS-REFERENCE TO RELATED APPLICATIONS

This application is the National Stage of International Application No. PCT/EP2009/060304, which designates the U.S., filed Aug. 7, 2009 which claims the benefit of Spanish Patent Application No. P200803623, filed Dec. 19, 2008, the contents of which are incorporated by reference herein.

This invention relates to use of estriol in the preparation of a pharmaceutical formulation for vaginal administration with the capacity to self-limit the absorption of estriol. This formulation is useful in the prevention and/or treatment of urogenital atrophy in women who have high probability of suffering or who suffer or have suffered from a cardiovascular pathology.

STATE OF THE ART

Estrogens and other female sex hormones are mainly produced in the ovaries and act throughout life on different tissues and organs. The cells of these organs, among which the breast and the uterus stand out, have receptors for estrogens and for other hormones. Estrogen hormones exert their action by binding to said receptors and starting different physiological or pathological processes. Among other physiological functions, they are responsible for the development and the modifications experienced by the breast and uterus in different life periods (puberty, pregnancy, lactation, menopause). But estrogens can also be involved in pathological processes, inducing, for example, coronary diseases, cerebrovascular accidents or thromboembolic diseases.

During the female climacteric, there is a progressive decrease of the production of estrogens by the ovaries which is usually accompanied by a series of signs, symptoms and pathologies. The main sign is the disappearance of menstruation (menopause) and the onset of multiple hormonal and psychic symptoms, vasomotor disorders (hot flashes and sweating) and urogenital atrophy being the most common.

When the production of estrogens decreases, there is a gradual decrease of the vaginal, urethral and vesical mucosa. When this atrophy becomes more pronounced, the genital symptoms—pruritus and vaginal burning, atrophic vaginitis, dyspareunia and trauma bleeding—and urological symptoms—repeated infections, dysuria and urinary incontinence-. Hormone deficiency furthermore triggers a decrease of the support tissue which can cause prolapses and stress urinary incontinence.

Although urogenital atrophy is a natural consequence of the climacteric and menopause, the associated disorders frequently affect the quality of life of the woman, therefore it is important for doctors to detect its presence early and indicate a treatment.

It must be taken into account that the symptoms of vaginal atrophy and the need for treatment are greater the older the postmenopausal woman is. However, the greater age, the probabilities of suffering from a cardiovascular pathology are greater, since the risk of suffering from a thromboembolic, coronary or cerebrovascular disease increases with age.

Despite the fact that estrogen therapy is usually very effective in reversing urogenital atrophy due to hormone deficiency, its use in women with vaginal atrophy who have a history of venous thromboembolic pathology (for example, deep vein thrombosis or pulmonary thromboembolism) or of coronary or cerebrovascular disease (such as myocardial infarction or ictus) is not recommended due to the risks that it entails. For the same reason, its use in women who have a high probability of suffering from a cardiovascular disease, as is the case of elderly postmenopausal women, is not recommended either.

Although urogenital atrophy due to estrogen deficiency does not always require systemic treatment by means of an oral hormone replacement therapy, but rather the administration of estrogens by vaginal route is preferred, it must be taken into account that this route is not risk-free. Locally administered estrogen hormones can be absorbed and pass to the systemic level, increasing the risk of causing coronary diseases, cerebrovascular accidents (ictuses) and/or thromboembolic diseases.

Estriol is one of the estrogens used in the treatment of urogenital atrophy, particularly by vaginal route. Currently marketed vaginal estriol formulations are usually administered in a dose of 0.5 mg/day (500 µg/day) for the first 2-3 weeks of treatment, followed by a dose of 0.5 mg 2 or 3 times/week but, due to the risks that it would entail, their administration in women who have suffered from or have a high probability of suffering from a cardiovascular disease is not recommended.

Consequently, the relief of urogenital atrophy due to estrogen deficiency in women who have suffered from a coronary disease, ictus or venous thromboembolic disease or who have a high probability of suffering from a cardiovascular disease is an issue that has still not been resolved. In particular, it is an unresolved problem in those postmenopausal women who are farther away from menopause, i.e., elderly women.

SUMMARY OF THE INVENTION

The inventors of the present invention have surprisingly found that certain vaginal estriol formulations form a system capable of self-limiting the absorption of estriol.

They have seen that, upon starting the treatment with the formulations of the present invention, when the vaginal epithelium is atrophic, there is a low absorption of estriol which is shown in an area under the curve (AUC) of plasma estriol concentration versus time of 1000 pg/ml×h, preferably less than 750 pg/ml×h. Once the repeated administration of these formulations has reversed vaginal atrophy, a fact which, surprisingly, occurs a few days (between 2 and 15 days, particularly between 2 and 10 days, more particularly between 2 and 7 days, even more particularly between 2 and 5 days) after starting the treatment, the absorption of estriol is insignificant and the area under the curve has decreased significantly with respect to the initial one, becoming less than 500 pg/ml×h, preferably less than 250 pg/ml×h. Therefore, the formulations of the present invention can be used without risk or a significantly reduced risk for the treatment or the prevention of urogenital atrophy in women with a high probability of suffering from a cardiovascular risk or in women who suffer or have suffered from a cardiovascular disease.

The inventors of the present invention have also surprisingly seen that, upon treating vaginal atrophy with commercially available formulations, the systemic exposure to estriol does not show significant changes throughout the treatment (although at the end the epithelium has become eutrophic) whereas, as already mentioned, upon treatment with the formulations of the present invention the systemic exposure decreases considerably during the treatment.

Consequently, the administration by vaginal route of the estriol formulations of the present invention allows preventing and/or treating urogenital atrophy due to estrogen deficiency while at the same time it achieves preventing or very significantly decreasing the risk associated with estrogen therapy of causing a cardiovascular disease.

Thus, a first aspect of the invention is the use of estriol in the preparation of a pharmaceutical formulation for vaginal administration with the capacity to self-limit the absorption of estriol, for the prevention and/or the treatment of urogenital atrophy in women, said women having a high probability of suffering from a cardiovascular pathology or suffering or having suffered from a cardiovascular pathology.

In other words, the present invention refers to a pharmaceutical formulation comprising estriol for vaginal administration with the capacity to self-limit the absorption of estriol, to be used in the prevention and/or the treatment of urogenital atrophy in women, said women having a high probability of suffering from a cardiovascular pathology or suffering or having suffered from a cardiovascular pathology.

A second aspect of the present invention relates to a method for preventing or treating the urogenital atrophy in women which comprises vaginally administering an estriol formulation with the capacity to self-limit the absorption of this hormone, said women having a high probability of suffering from a cardiovascular pathology or suffering or having suffered from a cardiovascular pathology.

BRIEF DESCRIPTION OF THE FIGURES

FIG. 1. Plasma estriol concentrations as a function of time.

DETAILED DESCRIPTION OF THE INVENTION

In the context of the present invention, women who have a history of a cardiovascular disease, and/or have at least one of established risk factors, namely: increasing age (for example woman above 50, or above 60 years), genetic susceptibility (for example, family history of cardiovascular disease, genetic mutations associated with cardiovascular diseases), concomitant pathologies (severe migraine with aura, high blood pressure, hypercholesterolemia, hypertriglyceridemia, insulin-dependent diabetes, cardiopathy, valvular heart disease etc.) and lifestyle (smoking, sedentariness, obesity, diet rich in fats, etc.), are considered to be women with a high probability of suffering from a cardiovascular disease (CVD).

More specifically, in the context of the present invention, cardiovascular pathologies include any disease or disorder of the cardiovascular system related to the action of estrogens or which could be considered as a contraindication of estrogen therapy. For example, coronary artery disease (or coronary cardiopathy), cerebrovascular accident (CVD or stroke), venous thromboembolic disease (VTD, comprising deep vein thrombosis and pulmonary embolism), superficial thrombophlebitis or thrombophilia.

Particularly, postmenopausal women, preferably older than 55, more preferably older than 60, even more preferably older than 65, constitute a population with an increased probability of suffering from a cardiovascular disease associated with estrogen therapy and can benefit from the treatment with the self-limiting formulations of the absorption of estriol of the present invention.

On the other hand, women who have a personal history of venous thromboembolic pathology (for example, deep vein thrombosis, pulmonary thromboembolism, superficial thromboflebitis or thrombophilia), of coronary or cerebrovascular disease (such as myocardial infarction or stroke) or of migraine with aura, can also benefit from the treatment with the self-limiting formulations of the absorption of estriol of the present invention.

It is clearly understood that when reference is made to "absorption of estriol", it is meant absorption of estriol into plasma.

An embodiment of the present invention relates to the use of said self-limiting formulations of the absorption of estriol in the prevention and/or the treatment of urogenital atrophy in women with a high probability of suffering from a cardiovascular pathology.

It also relates to the method of prevention and/or treatment of urogenital atrophy in women with a high probability of suffering from a cardiovascular disease using the self-limiting formulations of the absorption of estriol of the present invention.

A preferred embodiment relates to the use of said formulations in postmenopausal women far away from menopause (elderly women). In particular embodiments, said women had begun menopause at least 5 years, preferably 10, more preferably 15, even more preferably 20 years ago or more, at the beginning of the treatment.

Another embodiment relates to the use of said self-limiting formulations of the absorption of estriol in the prevention and/or the treatment of urogenital atrophy in women who suffer or have suffered from a cardiovascular pathology.

It also relates to the method of prevention and/or treatment of urogenital atrophy in women who suffer or have suffered from a cardiovascular disease using the self-limiting formulations of the absorption of estriol of the present invention.

A preferred embodiment relates to the use of said formulations in women, preferably postmenopausal women, who suffer or have suffered from a coronary disease, stroke, deep vein thrombosis, pulmonary embolism, superficial thromboflebitis, thrombophilia and/or severe migraine with aura.

Another embodiment also relates to a method for preventing the risk of suffering from a cardiovascular disease at systemic level associated with estrogen therapy which comprises vaginally administering an estriol formulation with the capacity to self-limit the absorption of this hormone.

As already mentioned, the pharmaceutical formulations useful in the method of treatment of the present invention are those which form a self-limiting system of the absorption of estriol. In the context of the present invention, a formulation with the capacity of self-limit the absorption of estriol is that one which provides a low absorption of hormone (estriol plasma peaks less than 150 pg/ml, preferably less than 125 pg/ml) when the vaginal mucosa is atrophic and insignificant absorption (which is shown in plasma estriol peaks close to baseline physiological values in postmenopausal women) once the atrophy has been reversed by the local action of estriol.

In particular, the pharmaceutical formulation can be any which, upon being vaginally administered, provides plasma estriol peaks less than 50 pg/ml, preferably less than 30 pg/ml, more preferably less than 25 pg/ml, even more preferably less than or equal to 20 pg/ml, after the repeated once daily administration for a time between 1 and 4 weeks, more particularly between 2 and 3 weeks, and after this period if the administration continues.

According to a preferred embodiment, the pharmaceutical formulation of the present invention can be any which enables a significant decrease of the systemic exposure to estriol (quantified using the AUC of plasma estriol concentrations as a function of time) after its repeated daily administration for several days once the vaginal atrophy has been reversed. In particular, it is any which provides an AUC less than 1000 pg/ml×h, preferably less than 750 pg/ml×h, more preferably less than 600 pg/ml×h, at the start of the treatment, more particularly in the first day of the treatment, and an AUC less than 750 pg/ml×h, preferably less than 500 pg/ml×h, more preferably less than 300 pg/ml×h, even more preferably less than 250 pg/ml×h, after the repeated once daily administration for a time between 1 and 4 weeks, particularly between 2 and 3 weeks, and after this period if the administration continues.

In an especially preferred embodiment, the pharmaceutical formulation of the present invention can be any which enables an almost insignificant systemic exposure once the urogenital atrophy has been reversed. It is particularly any which provides an AUC less than or equal to 150 pg/ml×h after the repeated once daily administration for a time between 1 and 4 weeks, preferably between 2 and 3 weeks, and after this period if the administration continues.

The pharmaceutical formulation can be, for example, in solid (pessaries, tablets, etc.), semisolid (gels, creams, etc.), liquid or foam form. And it can contain any of the excipients known by a person skilled in the art.

According to a preferred embodiment, the pharmaceutical compositions of the present invention are semisolid formulations, for example gels, cream gels or creams.

In a preferred embodiment, they are mucoadhesive gels, cream gels or creams containing at least one bioadhesive polymer (gelling agent and/or thickener) and an amount of estriol such that it allows administering less than 0.5 mg/day.

In a more preferred embodiment, the mucoadhesive formulations of the present invention contain at least two bioadhesive polymers and an amount of estriol such that it allows administering less than 0.3 mg/day, preferably less than 0.1 mg/day, still more preferably between 0.07 and 0.002 mg/day. For example, the formulations can contain estriol in an amount less than or equal to 0.03% by weight, preferably less than or equal to 0.01% by weight, more preferably between 0.007 and 0.0002% by weight, even more preferably between 0.005 and 0.001% by weight of the formulation.

The bioadhesive polymers useful for the formulations of the present invention are chosen from cellulose polymers, natural gums, sodium alginate, polyoxyethylenes, acrylic homo or copolymers, and mixtures thereof.

The cellulose polymers can be selected from methylcellulose, carboxymethylcellulose sodium (CMC), hydroxyethyl cellulose (HEC), hydroxypropyl cellulose (HPC) and hydroxypropyl methylcellulose (HPMC). The natural gums can be chosen, for example, from guar gum, karaya gum, xanthan gum and veegum. The acrylic polymers are preferably selected from polymers of the type of acrylic acid crosslinked with divinyl glycol (marketed under the trademark Noveon® AA-1 Polycarbophil) and polymers derived from acrylic acid crosslinked with allyl sucrose or allyl pentaerythritol designated as carbomer type polymers (marketed under the trademark Carbopol®).

Carbomer is the generic name adopted by a number of agencies, including the United States Pharmacopeia-National Formulary (USP-NF), United States Adopted Names Council (USAN) and the European Pharmacopoeia, for defining a various types of high molecular crosslinked acrylic acid-based polymers, which are marketed as Carbopol® polymers. U.S. Pat. Nos. 2,798,053, 4,267,103, 5,349,030, 4,996,274, 4,509,949, 5,373,044 describe these polyacrylic acid polymers, including the Carbopol® type, which are incorporated herein by reference. The "Handbook of Pharmaceutical Excipients", 2006, also describes the Carbopol® type polymers under the title "Carbomer", being this monograph also included herein by reference.

Carbomer type polymers and polycarbophil polymer are manufactured by cross-linking process. Depending upon the degree of cross-linking and manufacturing conditions, various grades of Carbopol are available. Carbopol® 934 P is cross-linked with allyl sucrose and is polymerized in solvent benzene. Carbopol 5984 EP is cross-linked with allyl sucrose and polimerized in ethyl acetate and cyclohexane. Carbopol® 71G, 971 P, 974 P are cross-linked with allyl pentaerythritol and polymerized in ethyl acetate. Carbopol® 980 and 981 are cross-linked with allyl penta-erythritol and polymerized in a cosolvent mixture of ethyl acetate and cyclohexane. Polycarbophil is cross-linked polymer in divinyl glycol and polymerized in solvent benzene or ethylacetate. All the polymers fabricated in ethyl acetate are neutralized by 1-3% potassium hydroxide.

Though Carbopol® 971 P and Carbopol® 974 P are manufactured by same process under similar conditions, the difference between them is that Carbopol® 971 P (USP29/NF24 Carbomer Homopolymer Type A) has slightly lower level of cross-linking agent than Carbopol® 974 P (USP29/NF24 Carbomer Homopolymer Type B). As a result, Carbopol® 971 P NF has a viscosity between 4000 and 11000 cP (measured in Brookfield RTV viscometer at 20 rpm, 25° C., in a 0.5% by weight mucilage, neutralized to pH 7.3-7.8), while Carbopol® 974 P NF has a viscosity between 29400 and 39400 cP (measured in Brookfield RTV viscometer at 20 rpm, 25° C., in a 0.5% by weight mucilage, neutralized to pH 7.3-7.8). For similar reasons, Carbopol® 981 NF has a viscosity between 4.000 and 10.000 cP (measured in Brookfield RTV viscometer at 20 rpm, 25° C., in a 0.5% by weight mucilage, neutralized to pH 7.3-7.8), while Carbopol® 980 NF has a viscosity between 40.000 and 60.000 cP (measured in Brookfield RTV viscometer at 20 rpm, 25° C., in a 0.5% by weight mucilage, neutralized to pH 7.3-7.8).

In an even more preferred embodiment, the mucoadhesive formulations used in the methods of the present invention contain at least one carbomer type polymer selected from polymers of acrylic acid crosslinked with allyl ethers of pentaerythritol, at least one polyacrylic acid crosslinked with civinylglycol and estriol in an amount such that it allows administering less than or equal to 0.1 mg/day.

The carbomer type polymer is preferably chosen from those whose synthesis does not require the use of benzene as solvent, such as Carbopol® 71G NF, Carbopol® 971P NF, Carbopol® 974P NF, Carbopol® 980 NF, Carbopol® 981 NF and Carbopol® 5984 EP. More preferably, the carbomer type polymer is chosen from those polymerized in ethyl acetate or in a mixture of ethyl acetate and cyclohexane. Even more preferably, the carbomer type polymer is chosen from those polymerized in ethyl acetate or in a mixture of ethyl acetate and cyclohexane and with a viscosity between 4.000 and 11.000 cP.

In a particularly preferred embodiment, the formulations contain at least two bioadhesive polymers, one is a carbomer type homopolymer selected from Carbopol® 971P NF and Carbopol® 981 NF and the other is Noveon® AA-1 Polycarbophil and an amount of estriol less than or equal to 0.03% by weight of the formulation.

In a more preferred embodiment the formulations contain at least Noveon® AA-1 Polycarbophil and Carbopol® 971P NF and an amount of estriol less than or equal to 0.03% by weight of the formulation.

Each of the polymers is incorporated in the amount necessary to provide the formulation with the physicochemical and organoleptic properties suitable for vaginal administration. In the case of acrylic polymers, the amount will be between 0.05 and 5% by weight of the formulation, preferably between 0.1 and 2%, more preferably between 0.25 and 1.5%.

The formulation can further contain other pharmaceutically acceptable excipients such as moisturizing agents, wetting agents, solubilizing agents, emulsifiers, preservatives, fatty or lipophilic substances, etc. in amounts known by a person skilled in the art.

Said formulations can be prepared by processes known by a person skilled in the art.

The formulations used in the methods of the present invention are preferably administered in an amount sufficient to form a layer over the entire vaginal surface and to obtain an effective and safe dosage regimen. For example, in the case of semisolid formulations, usually between 1 to 5 grams.

The devices which can be used for the administration of the semisolid formulations used in the method of the present invention are any of those one-dose or single-dose applicators known in the state of the art, for example an applicator with a plunger or with a bellows.

The dose of estriol to be administered to the patients treated with the methods of the present invention will be less than 0.5 mg/day, preferably less than 0.3 mg/day, more preferably less than 0.1 mg/day.

In a particular embodiment of the present invention, estriol is administered in doses between 0.002 and 0.07 mg/day (2 and 70 μg/day), preferably between 0.002 and 0.05 mg/day (2 and 50 μg/day), more preferably between 0.01 and 0.05 mg/day (10 and 50 μg/day), especially preferably between 0.02 and 0.05 mg/day (20 and 50 μg/day), for the prevention and/or the treatment of urogenital atrophy due to estrogen deficiency in women with a high probability of suffering from a cardiovascular pathology, preferably in postmenopausal women far away from menopause.

In another particular embodiment, estriol is administered in doses between 0.002 and 0.07 mg/day (2 and 70 μg/day), preferably between 0.002 and 0.05 mg/day (2 and 50 (g/day), more preferably between 0.01 and 0.05 mg/day (10 and 50 (g/day), especially preferably between 0.02 and 0.05 mg/day (20 and 50 (g/day), for the treatment of urogenital atrophy due to estrogen deficiency in women who have suffered or suffer from cardiovascular pathology, preferably in women having suffered or suffering coronary artery disease, cerebrovascular accident and venous thromboembolic disease.

Given the high safety of the formulations used in the methods of the present invention the treatment and/or the prevention of the vaginal atrophy can be performed simultaneously to the treatment of the cardiovascular disease.

The duration of the treatment and/or prevention of urogenital atrophy and the administration regimen of the present formulations will depend on the condition of the patient, the response to the treatment and the concomitant therapy. For example, a dose between 0.002 and 0.07 mg, preferably between 0.01 and 0.05 mg, a day for 2 or 3 weeks will be administered, and this will be continued with a dose between 0.002 and 0.07 mg, preferably between 0.01 and 0.05 mg, twice a week for the time necessary to maintain the trophic state of the vaginal mucosa, without interrupting the treatment. Alternatively, a dose between 0.002 and 0.07 mg, preferably between 0.01 and 0.05 mg, a day for 2 or 3 weeks will be administered, and this will be continued with a dose between 0.002 and 0.07 mg, preferably between 0.01 and 0.05 mg twice a week for a few weeks, for example between 6 and 10 weeks, thus interrupting the treatment until the symptoms appear again. Alternatively, given the high safety of the formulations used in the methods of the present invention, its administration could be continued with a daily, or a twice weekly, dose between 0.002 and 0.07 mg, preferably between 0.01 and 0.05 mg, for more than 3 weeks, or more than 10 weeks, respectively.

An illustrative example of the invention is described below. In no case should it be considered as limiting for the interpretation of the claims.

Assay

Comparative pharmacokinetics and efficacy of two estriol formulations of the invention versus a commercial estriol formulation (Ovestinon® cream, Organon) in postmenopausal women.

DESCRIPTION

The assayed formulations were two vaginal gels based on estriol T1 (0.002% ITFE) and T2 (0.005% ITFE) with the following composition:

| | Compound | amount | amount |
|---|---|---|---|
| Active ingredient | Estriol | 0.002% | 0.005% |
| Excipients | Carbopol ® 971(0.5%) | 2% | 2% |
| | Polycarbophil Noveon ® AA-1 (1.5%) | | |
| | Glycerin | 10% | 10% |
| | Methylparaben | 0.16% | 0.16% |
| | Propylparaben | 0.02% | 0.02% |
| | Sodium hydroxide | q.s. pH = 4.5 | q.s. pH = 4.5 |
| | Water | q.s. 100% | q.s. 100% |

These formulations were compared with a placebo formulation, without estriol, and a commercially available formulation (Ovestinon® cream, with 0.1% estriol).

Seventy postmenopausal women with vaginal atrophy participated in the assay, who were randomly distributed in four groups, 3 with 20 patients each and one with 10 patients:

The women received daily treatment for 21 consecutive days. 1 g of gel a day by vaginal route was administered to each patient of Groups B, C and D and 0.5 g of cream a day by vaginal route were administered to each patient of Group A.

| | |
|---|---|
| Group A: treated with Ovestinon (Reference-"R") | (n = 20) |
| Group B: treated with 0.005% ITFE | (n = 20) |
| Group C: treated with 0.002% ITFE | (n = 20) |
| Group D: treated with 0% ITFE (Placebo-"P") | (n = 10) |

The pharmacokinetic study was conducted in a subgroup of 42 women formed by 12 patients of each of the groups which were receiving active treatment (n=12 Group A, n=12 B, n=12 C).

The day before starting the treatment, the patients were subjected to a gynecological evaluation and to a cervical-vaginal cytology.

On the first day of treatment, the formulation corresponding to the assigned group was vaginally administered to all the patients and blood samples at time 0 (pre-dose), 0.5, 1, 2, 3, 4, 6, 8, 12 and 24 h (post-dose) were only extracted from the 42 volunteers of the pharmacokinetic study.

On the second day, the administration to all the patients was repeated and blood was only extracted from the 42 volunteers.

On days 3 to 20 of the treatment, the corresponding formulation was vaginally administered daily to all the patients. On days 7 and 14, subjective efficacy and tolerability immediately before the administration were evaluated.

On day 21, all the patients received the last dose of the treatment and blood samples at time 0 (pre-dose), 0.5, 1, 2, 3, 4, 6, 8, 12 and 24 h (post-dose) were only extracted from the 42 volunteers of the pharmacokinetic study. Local tolerability was evaluated 12 hours after the administration.

On day 22, all the patients were subjected to a gynecological evaluation and to a cervical-vaginal cytology and blood samples at the aforementioned times were only extracted from the 42 volunteers.

Assessment of the Effect on Vaginal Atrophy

The vaginal smears extracted during the gynecological evaluation of days 0 and 22 were fixed with a water-soluble solution for cytodiagnosis (ethanol/methanol EDTA) and stained according to the Papanicolaou technique for the qualitative evaluation of the cytological state and the count of superficial cells (SC), intermediate cells (IC) and parabasal cells (PC), which will be used in the subsequent determination of the maturation index (MI) and of the maturation value (MV).

The Maturation Value (MV) is calculated from the Maturation Index (MI) as follows=$0.2\times\%$ of parabasal cells+$0.6\times\%$ of intermediate cells+$1.0\times\%$ of superficial cells.

The data of the qualitative and quantitative assessments (MI and MV) are shown in Tables I, II and III It can therefore be concluded that the method of treatment of the present invention is effective in reversing vaginal atrophy.

Assessment of the Plasma Levels of Estriol

The plasma estriol concentration was determined by liquid chromatography/mass spectrometry (LC-MS/MS) in the blood samples extracted at time 0 (pre-dose), 0.5, 1, 2, 3, 4, 6, 8, 12 and 24 h (post-dose) on days 0, 1, 21 and 22 from the 42 volunteer patients.

The plasma levels obtained on the first day of treatment and on day 21 are shown in Tables IV and VI and in Graph 1.

The pharmacokinetic parameters calculated from these values are shown in Tables V and VII.

TABLE I

Frequency of the cytological pattern on day 0 (baseline level) and on day 22 (after the administration of formulations T1, T2, R or placebo).

| Cytological pattern | T1 Day 0 | T1 Day 22 | T2 Day 0 | T2 Day 22 | R Day 0 | R Day 22 | P Day 0 | P Day 22 |
|---|---|---|---|---|---|---|---|---|
| Atrophic | 7 | 1 | 7 | 0 | 7 | 0 | 2 | 2 |
| Slightly proliferative | 5 | 5 | 4 | 5 | 5 | 3 | 4 | 4 |
| Proliferative | 1 | 2 | 0 | 1 | 0 | 3 | 0 | 0 |
| Highly proliferative | 0 | 5 | 0 | 5 | 0 | 6 | 0 | 0 |
| Total | 13 | 13 | 11 | 11 | 12 | 12 | 6 | 6 |

TABLE IV

Plasma levels of estriol after the administration of a single dose of formulations T1, T2 and R. Day 1

| | Plasma levels of estriol: Mean value ± SD (pg/mL) | | |
|---|---|---|---|
| Time (h) | T1 | T2 | R |
| 0 | 1.48 ± 3.46 | 5.17 ± 17.90 | 10.33 ± 35.80 |
| 0.5 | 65.24 ± 45.54 | 87.59 ± 79.24 | 62.45 ± 78.01 |
| 1 | 72.43 ± 45.46 | 108.57 ± 79.76 | 83.36 ± 72.14 |
| 2 | 48.63 ± 25.79 | 105.20 ± 64.12 | 161.40 ± 98.58 |
| 3 | 35.53 ± 30.05 | 92.81 ± 64.15 | 180.88 ± 85.98 |
| 4 | 20.46 ± 12.27 | 57.78 ± 25.77 | 165.34 ± 68.88 |
| 6 | 5.57 ± 6.30 | 21.82 ± 17.83 | 106.43 ± 46.98 |
| 8 | 1.56 ± 3.67 | 9.02 ± 10.82 | 65.02 ± 52.91 |
| 12 | 1.65 ± 3.86 | 3.86 ± 10.02 | 34.20 ± 45.02 |
| 24 | 1.89 ± 5.12 | 3.85 ± 9.25 | 0.56 ± 1.92 |

TABLE II

Maturation index (MI) based on the differential count of superficial cells (SC), intermediate cells (IC) and parabasal cells (PC) on days 0 and 22 and difference with the baseline levels (ΔSC, ΔIC and ΔPC) after the administration of formulations T1, T2, R and P.

| | SCs/300: Mean value ± SD | | | ICs/300: Mean value ± SD | | | PCs/300: Mean value ± SD | | |
|---|---|---|---|---|---|---|---|---|---|
| | Day 0 | Day 22 | ΔSC | Day 0 | Day 22 | ΔIC | Day 0 | Day 22 | ΔPC |
| T1 | 12.92 ± 23.67 | 110.08 ± 79.80 | 97.15 ± 79.44 | 177.00 ± 117.11 | 174.00 ± 72.36 | −3.00 ± 107.71 | 110.08 ± 126.83 | 15.92 ± 43.98 | −94.15 ± 118.65 |
| T2 | 10.75 ± 12.17 | 111.25 ± 71.45 | 100.50 ± 76.84 | 207.00 ± 105.51 | 187.75 ± 71.25 | −19.25 ± 71.38 | 82.25 ± 112.73 | 1.00 ± 3.46 | −81.25 ± 111.46 |
| R | 9.50 ± 14.00 | 150.75 ± 73.55 | 141.25 ± 66.39 | 209.00 ± 95.82 | 149.25 ± 73.55 | 59.75 ± 126.06 | 81.50 ± 102.24 | 0.00 ± 0.00 | −81.50 ± 102.24 |
| P | 15.50 ± 14.63 | 23.00 ± 18.26 | 7.50 ± 4.55 | 198.00 ± 123.90 | 206.50 ± 94.21 | 8.50 ± 34.12 | 86.50 ± 135.48 | 70.50 ± 109.2 | −16.00 ± 32.40 |

TABLE III

Maturation value (MV) on days 0 and 22 and difference with the baseline level (ΔMV) after the administration of formulations T1, T2, R and P.

| | MV: Mean value ± SD | | |
|---|---|---|---|
| Treatment | Day 0 | Day 22 | ΔMV |
| T1 | 47.12 ± 18.73 | 72.51 ± 14.34 | 25.38 ± 22.85 |
| T2 | 50.13 ± 15.89 | 74.70 ± 9.57 | 24.57 ± 23.43 |
| R | 50.50 ± 14.47 | 80.08 ± 9.84 | 29.58 ± 15.63 |
| P | 50.53 ± 19.68 | 53.67 ± 16.68 | 3.13 ± 4.17 |

TABLE V

Pharmacokinetic parameters (±SD) of estriol after the administration of a daily single dose of formulations T1, T2 and R. Day 1

| | $C_{max}$ (pg/mL) Corrected dose | $T_{max}$ (h) | $AUC_{0-t}$ (pg/mL × h) Corrected dose | $AUC_{0-\infty}$ (pg/mL × h) Corrected dose | $t_{1/2}$ (h) | MRT (h) |
|---|---|---|---|---|---|---|
| T1 | 60.57 ± 27. | 1.29 ± 0 | 171.65 ± 80 | 194.29 ± 73 | 1.59 ± | 3.99 ± |
| T2 | 106.40 ± 63 | 2.38 ± 1 | 406.75 ± 19 | 461.53 ± 17 | 1.65 ± | 4.57 ± |

TABLE V-continued

Pharmacokinetic parameters (±SD) of estriol after the administration of a daily single dose of formulations T1, T2 and R. Day 1

| | $C_{max}$ (pg/mL) Corrected dose | $T_{max}$ (h) | $AUC_{0-t}$ (pg/mL × h) Corrected dose | $AUC_{0-\infty}$ (pg/mL × h) Corrected dose | $t_{1/2}$ (h) | MRT (h) |
|---|---|---|---|---|---|---|
| R | 210.06 ± 82 | 3.04 ± 1 | 1221.97 ± 5 | 1431.21 ± 8 | 2.52± | 5.79± |

TABLE VI

Plasma levels of estriol after the administration of daily doses of formulations T1, T2 and R. Day 21

| | Plasma levels of estriol: Mean value ± SD (pg/mL) | | |
|---|---|---|---|
| Time (h) | T1 | T2 | R |
| 0 | BLQL | BLQL | 4.98 ± 6.45 |
| 0.5 | 5.18 ± 8.07 | 2.48 ± 6.14 | 4.92 ± 6.54 |
| 1 | 8.40 ± 10.29 | 10.56 ± 14.39 | 7.33 ± 8.28 |
| 2 | 11.20 ± 9.92 | 17.79 ± 17.01 | 23.94 ± 11.60 |
| 3 | 13.00 ± 7.25 | 19.32 ± 13.88 | 38.58 ± 21.40 |
| 4 | 8.47 ± 6.28 | 16.30 ± 9.16 | 60.08 ± 25.51 |
| 6 | 1.63 ± 4.21 | 7.28 ± 5.62 | 72.36 ± 39.18 |
| 8 | 0.87 ± 3.00 | 1.85 ± 3.43 | 76.17 ± 34.78 |
| 12 | BLQL | BLQL | 74.81 ± 41.68 |
| 24 | BLQL | BLQL | 3.47 ± 7.40 |

BLQL = below the lower quantification limit (5 pg/mL)

TABLE VII

Pharmacokinetic parameters (±SD) of estriol after the administration of daily doses of formulations T1, T2 and R. Day 21

| | $C_{ssmax}$ (pg/mL) Corrected dose | $T_{ssmax}$ (h) | $C_{ssmin}$ (pg/mL) | $AUC_{ssmax}$ (pg/mL × h) Corrected dose |
|---|---|---|---|---|
| T1 | 13.77 ± 8.03 | 2.17 ± 0.94 | 0.0 ± 0.0 | 36.33 ± 30.52 |
| T2 | 22.80 ± 15.78 | 3.25 ± 1.14 | 0.0 ± 0.0 | 73.71 ± 46.86 |
| R | 89.95 ± 38.55 | 7.67 ± 3.06 | 2.97 ± 5.49 | 800.11 ± 363.51 |

It can therefore be concluded that the safety profile of the formulations of the present invention is highly favorable since the systemic exposure to estriol after repeated administration is almost insignificant (extremely low). Additionally, the systemic exposure is significantly lower than that occurring after the administration of the reference product.

In addition, although the systemic exposure to estriol is significantly lower, the formulations of the present invention cause a similar increase of the maturation value on day 22 compared to day 0, indicating an effect similar to that of the reference product in vaginal mucosa.

The invention claimed is:

1. A method of treatment of urogenital atrophy in woman comprising the vaginal administration of pharmaceutical estriol formulations with the capacity of self-limiting the absorption of estriol to a woman in need thereof, wherein said women suffer or have suffered a venous thromboembolic pathology, a coronary or cerebrovascular disease or migraine with aura and wherein the pharmaceutical formulation provides a dose of estriol less than or equal to 0.3 mg/day.

2. The method according to claim 1, wherein the pharmaceutical formulation provides an area under the curve less than 300 pg/ml×h.

3. The method according to claim 2, wherein the pharmaceutical formulation provides an area under the curve less than 250 pg/ml×h.

4. The method according to claim 3, wherein the pharmaceutical formulation provides an area under the curve less than or equal to 150 pg/ml×h after the administration of repeated once daily doses for a time between 2 and 3 weeks.

5. The method according to claim 1, wherein the pharmaceutical formulation provides plasma levels of estriol less than 50 pg/ml after the repeated once daily administration for a time between 1 and 4 weeks.

6. The method according to claim 5, wherein the pharmaceutical formulation provides plasma levels of estriol less than 25 pg/ml after the repeated once daily administration for a time between 2 and 3 weeks.

7. The method according to claim 6, wherein the pharmaceutical formulation provides plasma levels of estriol less than or equal to 20 pg/ml.

8. The method according to claim 1, wherein the absorption of estriol is low when the vaginal epithelium is atrophic and the absorption of estriol becomes insignificant once the repeated administration of the formulation has reversed the vaginal atrophy.

9. The method according to claim 8, wherein the area under the curve of plasma estriol concentration versus time is less than 1000 pg/ml×h when the vaginal epithelium is atrophic, and less than 500 pg/ml×h once vaginal atrophy has been reversed.

10. The method according to claim 9, wherein the area under the curve of plasma estriol concentration versus time is less than 750 pg/ml×h when the vaginal epithelium is atrophic, and less than 250 pg/ml×h once vaginal atrophy has been reversed.

11. The method according to claim 8, wherein vaginal atrophy is reversed between 2 and 10 days, more particularly between 2 and 7 days, even more particularly between 2 and 5 days after the beginning of the treatment.

12. The method according to claim 1, wherein the women suffer or have suffered from a coronary disease, stroke, deep vein thrombosis, pulmonary embolism, superficial thrombophlebitis, thrombophilia and/or severe migraine with aura.

13. The method according to claim 1, wherein the dose of estriol is less than or equal to 0.1 mg/day.

14. The method according to claim 13, wherein the dose of estriol is between 0.002 and 0.07 mg/day.

15. The method according to claim 14, wherein the dose of estriol is between 0.01 and 0.05 mg/day.

16. The method according to claim 1, wherein the pharmaceutical formulation is a mucoadhesive gel, cream gel or cream containing at least one bioadhesive polymer.

17. The method according to claim 16, wherein said bioadhesive polymer is selected from the group consisting of cellulose polymers, natural gums, sodium alginate, polyoxyethylenes, acrylic polymers and mixtures thereof.

18. The method according to claim 17, wherein said bioadhesive polymer is selected from the group consisting of methylcellulose, carboxymethylcellulose sodium (CMC), hydroxyethyl cellulose (HEC), hydroxypropyl cellulose (HPC) and hydroxypropyl methylcellulose (HPMC).

19. The method according to claim 17, wherein said bioadhesive polymer is selected from the group consisting of polymers of the type of acrylic acid crosslinked with divinyl glycol and polymers derived from acrylic acid crosslinked with allyl sucrose or allyl pentaerythritol.

20. The method according to claim 19, wherein the amounts of said acrylic polymer crosslinked with divinyl glycol and/or said polymers derived from acrylic acid crosslinked with allyl ethers of sucrose or allyl ethers of pentaerythritol are individually comprised between 0.05 and 5% by weight of the formulation, preferably between 0.1 and 2%, more preferably between 0.25 and 1.5%.

21. The method according to claim 16 wherein the pharmaceutical formulation contains at least one polyacrylic acid crosslinked with divinyl glycol and at least one polymer of acrylic acid crosslinked with allyl ethers of penta-erythritol.

22. The method according to claim 21, wherein the acrylic acid crosslinked with allyl ethers of penta-erythritol are those polymerized in ethyl acetate or in a mixture of ethyl acetate and cyclohexane.

23. The method according to claim 22, wherein the acrylic acid crosslinked with allyl ethers of pentaerythritol and polymerized in ethyl acetate or in a mixture of ethyl acetate and cyclohexane has a viscosity between 4.000 and 11.000 cP.

24. A method of using estriol in the preparation of a pharmaceutical formulation for vaginal administration with the capacity to self-limit the absorption of estriol, for the treatment of urogenital atrophy in women who suffer or have suffered a venous thromboembolic pathology, a coronary or cerebrovascular disease or migraine with aura and wherein the pharmaceutical formulation provides a dose of estriol less than or equal to 0.3 mg/day.

\* \* \* \* \*